(12) United States Patent
Hernandez

(10) Patent No.: US 9,241,701 B2
(45) Date of Patent: Jan. 26, 2016

(54) CANNULA SYSTEM AND METHOD FOR PARTIAL THICKNESS ROTATOR CUFF REPAIR

(75) Inventor: Joseph Hernandez, Raynham, MA (US)

(73) Assignee: DePuy Mitek, Inc., Raynham, MA (US)

( * ) Notice: Subject to any disclaimer, the term of this patent is extended or adjusted under 35 U.S.C. 154(b) by 1007 days.

(21) Appl. No.: 13/249,733

(22) Filed: Sep. 30, 2011

(65) Prior Publication Data
US 2012/0123473 A1 May 17, 2012

Related U.S. Application Data

(60) Provisional application No. 61/412,579, filed on Nov. 11, 2010.

(51) Int. Cl.
A61B 17/04 (2006.01)
A61F 2/08 (2006.01)

(52) U.S. Cl.
CPC ....... A61B 17/0401 (2013.01); *A61B 2017/044* (2013.01); *A61B 2017/0409* (2013.01); *A61F 2/0805* (2013.01); *A61F 2002/0858* (2013.01); *A61F 2002/0888* (2013.01)

(58) Field of Classification Search
CPC .......................... A61B 17/0401; A61F 2/0811
USPC .......... 606/148, 151, 232; 600/184, 201, 214, 600/219, 224
See application file for complete search history.

(56) References Cited

U.S. PATENT DOCUMENTS

| | | | |
|---|---|---|---|
| 4,716,901 | A | 1/1988 | Jackson |
| 4,872,451 | A | 10/1989 | Moore et al. |
| 5,334,198 | A | 8/1994 | Hart |
| 5,431,676 | A | 7/1995 | Dubrul |
| 5,891,159 | A | 4/1999 | Sherman |
| 7,381,213 | B2 | 6/2008 | Lizardi |
| 2003/0073934 | A1 | 4/2003 | Putz |
| 2004/0039266 | A1 | 2/2004 | Hillier |
| 2008/0015408 | A1 | 1/2008 | Paulitto et al. |
| 2008/0033486 | A1 | 2/2008 | Whittaker |
| 2008/0147063 | A1 | 6/2008 | Cauldwell |
| 2008/0228251 | A1 | 9/2008 | Hill |

(Continued)

FOREIGN PATENT DOCUMENTS

WO WO 2005/122954 A1 12/2005

OTHER PUBLICATIONS

Millstein, Eric S. et al., Arthroscopic Management of Partial, Full-Thickness, and Complex Rotator Cuff Tears: Indication, Techniques, and Complications, Arthroscopy: The Journal of Arthroscopic and Related Surgery, Dec. 2003, pp. 189-199, vol. 19, No. 10.

(Continued)

*Primary Examiner* — Thomas McEvoy

(57) ABSTRACT

A trans-soft tissue anchor implantation system in one embodiment includes a positioning wire having a tissue penetrating distal tip, a cannula for passage through the soft tissue and a suture anchor. The cannula has an axial lumen therethrough sized to accommodate at least the positioning wire, a thin-walled distal portion and a tissue engaging feature, such as an arcuate groove, on at least a portion of an outer surface of the cannula proximal of and adjacent to the distal portion. Tissue, such as a tendon, expands into the groove allowing a surgeon to manipulate the tissue with the cannula.

16 Claims, 14 Drawing Sheets

(56) References Cited

U.S. PATENT DOCUMENTS

| | | | |
|---|---|---|---|
| 2009/0312782 A1 | 12/2009 | Park | |
| 2010/0081885 A1* | 4/2010 | Wing et al. | 600/215 |
| 2010/0240961 A1* | 9/2010 | Aferzon | 600/212 |
| 2011/0106013 A1* | 5/2011 | Whittaker et al. | 604/174 |

OTHER PUBLICATIONS

Waibl, Bernhard et al., Partial-Thickness Articular Surface Supraspinatus Tears: A New Transtendon Suture Technique, Arthroscopy: The Journal of Arthroscopic and Related Surgery, Mar. 2005, pp. 376-381, vol. 21, No. 3.

Lo, Ian K.Y., et al., Transtendon Arthroscopic Repair of Partial-Thickness, Articular Surface Tears of the Rotator Cuff, Arthroscopy: The Journal of Arthroscopic and Related Surgery, Feb. 2004, pp. 214-220, vol. 20, No. 2.

Fox, Jeff A. et al., Pasta Lesion-Trans-Tendon Technique for Repair, Operative Techniques in Orthopaedics, 2002, pp. 191-196, vol. 12, No. 3.

Porat, Sharoun et al., Repair of partial thickness rotator cuff tears: A retrospective review with minimum two-year follow-up, J Shoulder Elbow Surg, 2008, pp. 727-721, vol. 17, No. 5.

Gonzalez-Lomas, Guillem et al., In situ transtendon repair outperforms tear completion and repair for partial articular-sided supraspinatus tendon tears, J Shoulder Elbow Surg, Sep./Oct. 2008, pp. 722-728, vol. 17, No. 5.

Brockmeier, Stephen F. et al., Arthroscopic Intratendinous Repair of the Delaminated Partial-Thickness Rotator Cuff Tear in Overhead Athletes, Arthroscopy: The Journal of Arthroscopic and Related Surgery, Aug. 2008, pp. 961-965, vol. 24, No. 8.

\* cited by examiner

CANNULA SYSTEM AND METHOD FOR PARTIAL THICKNESS ROTATOR CUFF REPAIR

BACKGROUND

The present application relates to systems and methods for performing a repair of soft tissue to bone, particularly a partial thickness rotator cuff tear.

A common injury, especially among athletes, is the complete or partial detachment of tendons, ligaments or other soft tissues from bone. Tissue detachment may occur during a fall, by overexertion, or for a variety of other reasons. Surgical intervention is often needed, particularly when tissue is mostly or completely detached from its associated bone. Currently available devices for tissue attachment include screws, staples, suture anchors and tacks.

Arthroscopic tissue attachment is commonly practiced in shoulder rotator cuff and instability procedures utilizing at least one cannula. Typically, an anchor loaded with suture is fixated to bone using an inserter-type device. The suture is normally slidably attached to the anchor through an eyelet or around a post, such that a single length of suture has two free limbs. The suture limbs typically are carried along the exterior of the inserter, usually within a groove or other exterior channel, or within the interior of the inserter. After the anchor is inserted into the bone, one limb of the suture is passed through soft tissue to be repaired such as a tendon or labrum. The two ends of the suture are then tied to each other, thereby capturing the soft tissue in a loop with the anchor. Upon tightening the loop, the soft tissue is approximated to the bone via the anchor.

A PASTA (Partial Articular Surface Tendon Avulsion, also known as Partial Articular Sided Tendon Avulsion) lesion in a rotator cuff of a shoulder can be particularly difficult to repair. The rotator cuff comprises a group of muscles which surround the shoulder and tendons which attach those muscles to the humeral head. The tendons have a footprint where they attach to the humeral head and, in a PASTA lesion, a portion of the articular side of the rotator cuff tendon's footprint becomes detached from the humeral head. Such lesions are most commonly found on the supraspinatus tendon.

One option for treatment is completion of the partial tear and then completion of a repair using standard techniques for a full thickness tear. Preservation of the existing, healthy tissue attachment is thus lost and the entire tendon must be reattached. Another option includes screwing a threaded suture anchor through the tendon and into the humeral head, passing suture through the tendon and tying down the tendon to effect reattachment. This causes further trauma to the tendon.

There has been a long-felt need to provide a surgeon with access through soft tissue without excessively damaging the soft tissue. A number of early access devices including radially expandable dilators are disclosed by Dubrul et al. in U.S. Pat. No. 5,431,676. An appliance for forming an opening through skin is described by Jackson et al. in U.S. Pat. No. 4,716,901.

A more recent cannula device is disclosed by Putz in U.S. Patent Publication No. 2003/0073934. Two cannulas having side gaps are aligned without the side gaps juxtaposed to define a passage for a probe. The cannulas are then rotated relative to each other to facilitate separation from the probe.

It is therefore desirable to have an improved cannula system to minimize trauma to soft tissue while accessing bone.

SUMMARY OF THE INVENTION

An object of the present invention is to provide improved access to bone through soft tissue such as a tendon.

Another object of the invention is to enhance manipulation of the soft tissue.

This invention features a trans-soft tissue anchor implantation system including, in one embodiment, a positioning wire having a tissue penetrating distal tip, a cannula for passage through the soft tissue and a suture anchor. The cannula has an axial lumen therethrough sized to accommodate at least the positioning wire, a thin-walled, preferably sharp, distal portion and a tissue engaging feature, such as an arcuate groove, indentation or other recess, which is annular in some embodiments, on at least a portion of an outer surface of the cannula proximal of and adjacent to the distal portion. Tissue, such as a tendon, expands into the groove allowing a surgeon to manipulate the tissue with the cannula.

In some embodiments, the system further includes an obturator having a distal tip, which is sharp in one embodiment and is blunt in other embodiments. Preferably, the obturator includes a central lumen having a longitudinal axis and sized to accommodate the positioning wire, and the distal tip of the obturator is laterally offset from the longitudinal axis of the central lumen. Preferably, the offset remains within a nominal radius of the central lumen.

Also featured is a cannula having a first curved section having a first thin-walled distal portion and a second curved section having a second thin-walled distal portion, the first and second curved sections capable of being moved relative to each other from an initial, low-profile configuration, with the second section nesting at least partially within the first section to present less than a full circumference of cannula to the soft tissue, to a second, larger configuration defining an axial cannula lumen therethrough.

In certain embodiments, at least one tissue engaging feature such as an arcuate groove is defined on at least a portion of at least one of the first and second curved sections. In one embodiment, at least a portion of the tissue engaging feature is protected relative to the tissue in the initial configuration and is exposed to the tissue in the second configuration. In some embodiments, at least one of the first and second distal portions has an angled distal surface to progressively, in a proximal direction extending away from a distal end of that distal portion, increase the surface area of initial contact with and then penetration into the soft tissue, and at least one of the first and second distal portions has a distal edge which is sufficiently sharp to be capable of cutting through a tendon.

This invention further features a method for passing a suture anchor through a soft tissue and into a bone, by locating a desired anchor receiving site on the bone, passing a locating wire through the soft tissue and at least onto the bone at the anchor receiving site, and passing over the locating wire and through the soft tissue a cannula which comprises a thin-walled distal portion and an axial lumen therethrough sized to accommodate the positioning wire. The method further includes engaging a portion of the soft tissue with a tissue engaging feature on at least a portion of an outer surface of the cannula proximal of and adjacent to the thin-walled distal portion, and then manipulating the tissue with the cannula. A suture anchor is passed through the cannula and placed into the bone at the anchor site.

In some embodiments, the method includes passing the cannula through the tissue while it is in an initial, low-profile configuration with a second curved section of the cannula being nested within a first curved section of the cannula to present less than a full circumference of cannula to the soft tissue. The first and second curved sections are then moved relative to each other to a second, larger configuration defining the axial cannula lumen therethrough. In certain embodiments, the method further includes manipulating the tissue with the cannula after the first and second curved sections are moved to the second configuration.

BRIEF DESCRIPTION OF THE DRAWINGS

In what follows, preferred embodiments of the invention are explained in more detail with reference to the drawings, in which.

DETAILED DESCRIPTION

This invention may be accomplished by a trans-soft tissue anchor implantation system including, in one construction, a positioning wire having a tissue penetrating distal tip, a cannula for passage through the soft tissue and a suture anchor. The cannula has an axial lumen therethrough sized to accommodate at least the positioning wire, a thin-walled, preferably sharp distal portion and, preferably, a tissue engaging feature, such as an arcuate groove, indentation or other recess, on at least a portion of an outer surface of the cannula proximal of and adjacent to the distal portion. Tissue, such as a tendon, expands into the groove allowing a surgeon to manipulate the tissue with the cannula. Cannulas with tissue engaging features according to the present invention are shown beginning with FIG. 12. Cannulas with first and second curved sections according to the present invention, with the second section nesting at least partially within the first section to present less than a full circumference of cannula to the soft tissue, are illustrated beginning with FIG. 21.

Figure 1:
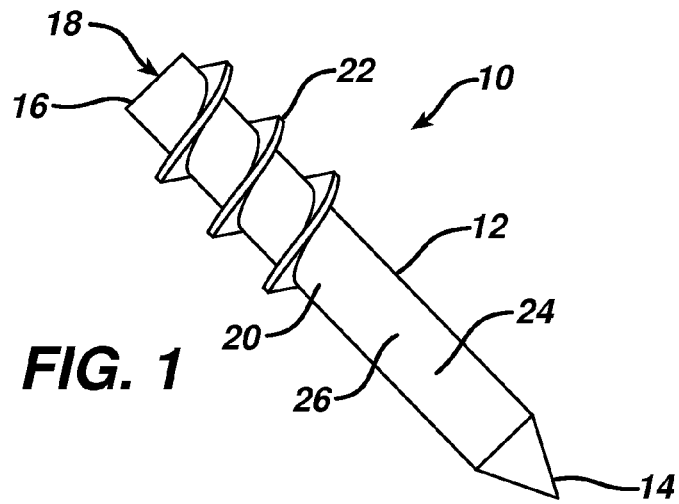
FIG. 1 is a perspective view of a novel suture anchor.

FIG. 1 depicts a novel suture anchor 10, for use with a novel cannula system and method, with an elongated body 12 having a pointed distal tip 14 and a proximal end 16. An axial passageway 18 extends into the body 12 from the proximal end 16. The passageway 18 is open along its sides 20. A thread 22 encircles the body 12. A suture bridge or post 24, FIG. 2, spans the passageway 18 laterally at a distal portion 26 thereof.

Figure 2:
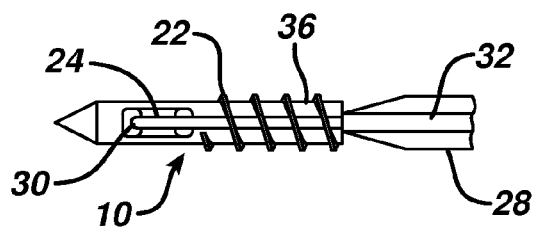
FIG. 2 is a side elevation view of the suture anchor of FIG. 1 loaded onto a driver.
Figure 3:
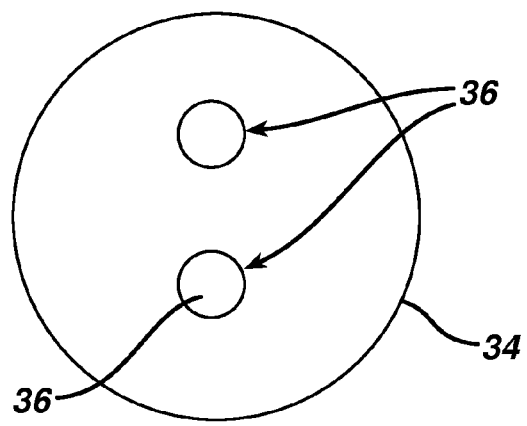
FIG. 3 is a top plan view of the suture anchor of FIG. 1.

Turning also now to FIGS. 2 and 3, an inserter 28 fits into the passageway 18. A length of suture 30 passes around the suture bridge 24 and is received within longitudinal grooves 32 on the inserter 28. As best seen in FIG. 3, the cross-sectional shape of the passageway 18 at the proximal end 16 is essentially a hexagon 34 with a pair of suture passages 36 on opposite corners thereof. The suture passages 36 lead to either side of the suture bridge 24. The inserter 28 has a complimentary shape to fit within the hexagon 34 with its grooves 32 in alignment with the suture passages 36 on the anchor 10.

The suture anchor 10 as shown with the suture passages 36 penetrating the body 12 to leave the passageway 18 open except for the thread 22 minimizes its cross section to provide the least trauma to soft tissue through which it will pass while still having sufficient mechanical strength for the driver 28 to drive it into bone. Where additional fixation strength within the bone may be required the cross section of the anchor 10 could be enlarged, in which case the suture passages 36 need then not necessarily penetrate the body 12 laterally. The anchor 10 can be formed of any suitable biocompatible material such as stainless steel, titanium, cobalt chrome, PEEK (polyaryletheretherketone), Biocryl Rapide polymer, other biocompatible polymers, polymer-ceramic composites, bioabsorbable polymers and the like. Suitable anchor materials and configurations include those disclosed by Cauldwell et al. in U.S. Patent Publication No. 2008/0147063 and in U.S. Pat. No. 7,381,213 by Lizardi, both of which are incorporated herein by reference in their entireties.

Figure 4:
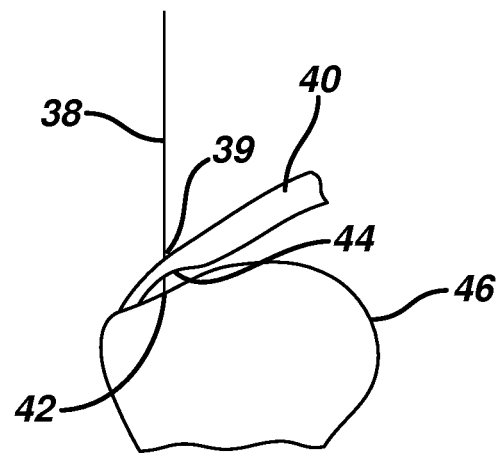
FIG. 4. is a side elevation view of a humerus and associated rotator cuff tendon suffering a PASTA lesion showing a K wire being inserted through the tendon to a desired location for placing a suture anchor.

FIGS. 4 to 11 illustrate a procedure to repair a PASTA lesion using the suture anchor 10 of FIG. 1 and a novel cannula system 48. As seen in FIG. 4, either percutaneously or arthroscopically, a Kirschner wire (K wire) 38, also known as a type of positioning wire or locating wire, is inserted at a first location 39 through a tendon 40 of a rotator cuff to a desired anchor site 42 beneath its attachment footprint 44 and positioned upon an associated humeral head 46. The K wire 38 can be tapped into the bone or merely positioned at the site 42; in other words, the wire is positioned at least onto the bone at a desired location. To ease manipulation of the K wire 38 it is preferably textured on its outer surface and may be provided with a removable proximal handle (not shown). This site 42 on the humeral head 46 is where the suture anchor 10, FIG. 1, will be implanted.

Figure 5:
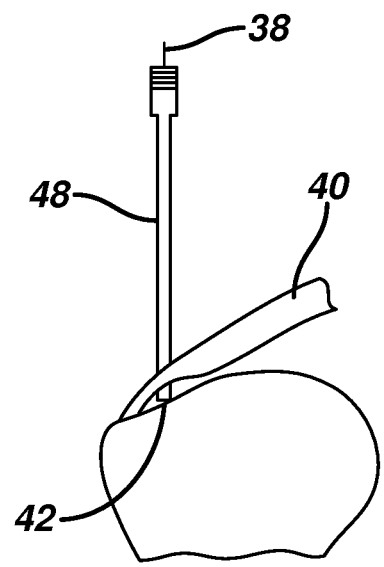
FIG. 5. is a side elevation view of the tendon of FIG. 4 showing a novel cannula system being passed through the tendon over the K wire.
Figure 6:
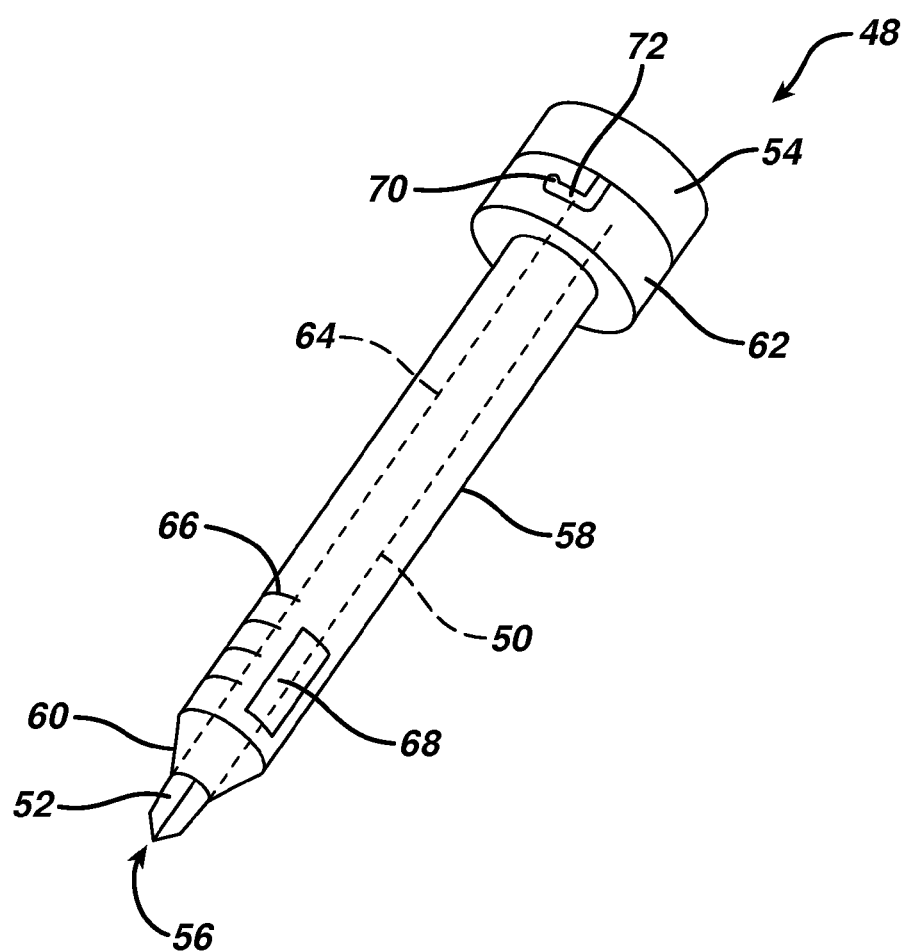
FIG. 6 is a perspective view of the cannula system of FIG. 5.
Figure 6A:
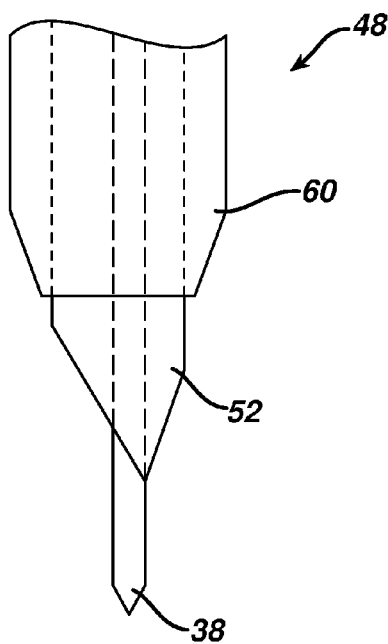
FIG. 6A is an enlarged side view of the distal portion of the cannula system of FIG. 6.
Figure 6B:
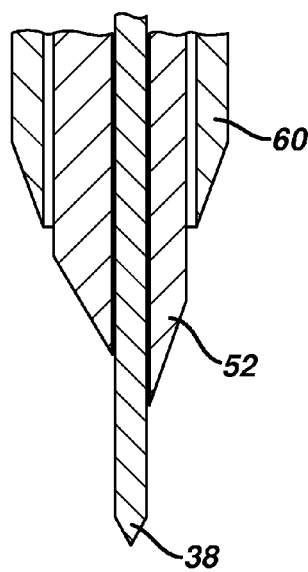
FIG. 6B is a cross-sectional view of the cannula system of FIG. 6A.
Figure 6C:
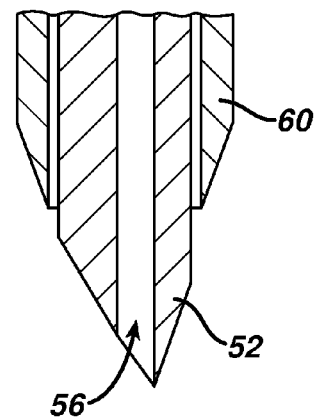
FIG. 6C is a view similar to FIG. 6B with the K wire removed.

As seen in FIG. 5, cannula system 48 is passed over the K wire 38 and through the tendon 40 to the site 42. FIG. 6 shows the cannula 48 in more detail for one construction, with enlargements of the distal portion illustrated in FIGS. 6A-C. Cannula 48 comprises an inner cannula 50 having a sharp distal portion 52, proximal handle 54 and a lumen 56 therethrough, FIG. 6C. The inner cannula 50 fits within an outer cannula 58 which has a distal end 60, proximal handle 62 and lumen 64 therethrough. The distal portion 52 of the inner cannula 50 extends slightly beyond the distal end 60 of the outer cannula 58 and the distal end 60 is tapered so that rather than core through the tendon 40 the distal portion 52 creates a small hole and the tapering on the distal portion 52 and distal end 60 allow the cannula system 48 to push aside the tissue and create the smaller hole through the tendon 40 with the least damage thereto, in other words, with less cutting of soft tissue. Prior cannulas were inserted through a slit cut into the tissue. The cannula system 48 dilates the tissue gently to minimize trauma to the tissue. The outer cannula 58 has lines 66 which provide a visual indication of depth penetration and also a visualization window 68 which aids in anchor insertion and assessment of appropriate depth into the bone. To prevent slippage of the inner cannula 50 relative to the outer cannula 58 during insertion so provision is preferably provided to help keep them together. Shown are an interlocking nub 70 and groove 72, but other options such as a friction fit, threading, or magnets are employed in other constructions.

Figure 7:
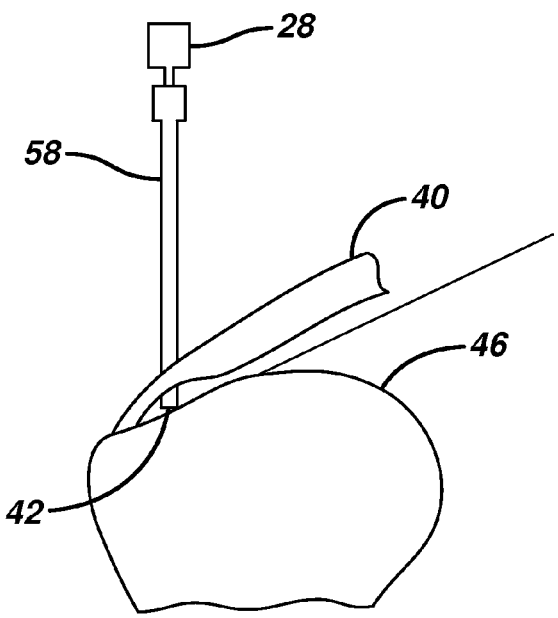
FIG. 7 is a side elevation view of the tendon of FIG. 4 with a suture anchor loaded onto a driver, such as shown in FIG. 2, being passed through the tendon via an outer portion of the cannula system.
Figure 8:
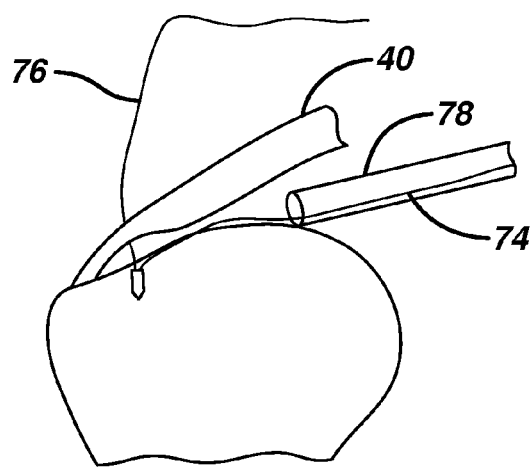
FIG. 8 is a side elevation view of the tendon of FIG. 4 showing the suture anchor implanted into the humerus beneath the tendon and a limb of suture passing from the suture anchor out of an anterior cannula.

As seen in FIG. 7, in preparation for insertion of the anchor 10, the K wire 38 and inner cannula 50 are removed leaving the outer cannula 58 positioned at the anchor site 42. The suture anchor 10 is preloaded onto the inserter 28, with the suture 30 in place around the suture bridge 24 and passing through the suture passages 36 and grooves 32 (see FIG. 2), is passed down through the outer cannula lumen 60 to the anchor site 42 and is then driven into the humeral head 46. If the anchor 10 is formed of a biocompatible metal such as stainless steel or titanium it can be simply twisted in via the inserter 28. If instead it is formed of a bioabsorbable polymer or other material having less strength a pilot hole should be prepared such as with a drill, tap or awl, at the site 42 through the cannula 46 prior to inserting the anchor 10 through the lumen 60. The inserter 28 and outer cannula 58 can then be removed leaving first and second suture limbs, 74 and 76 respectively, passed up through the tendon 40 at the first location 39 through which the cannula 48 had passed. As seen in FIG. 8, the first suture limb 74 is then retrieved through an auxiliary cannula 78 such as via a grasper (not shown).

Figure 9:
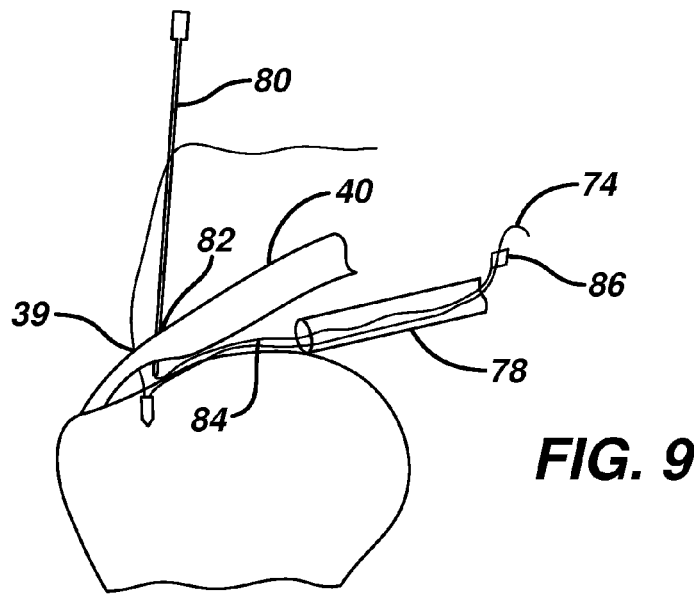
FIG. 9 is a side elevation of the tendon of FIG. 4 showing a spinal needle passed through a location on the tendon and a suture retriever being passed through the spinal needle and out of the anterior cannula.
Figure 10:
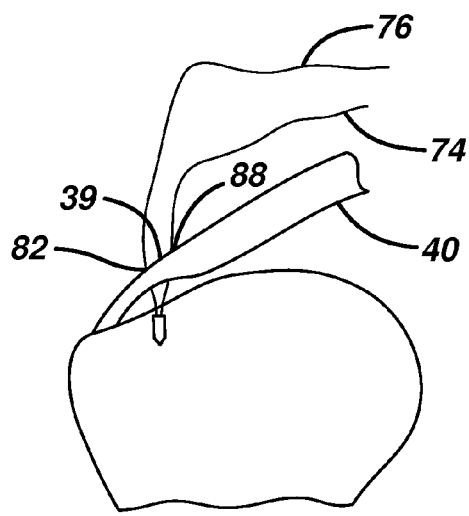
FIG. 10 is a side elevation of the tendon of FIG. 4 showing both suture limbs passed from the suture anchor and through the tendon at different locations.
Figure 11:
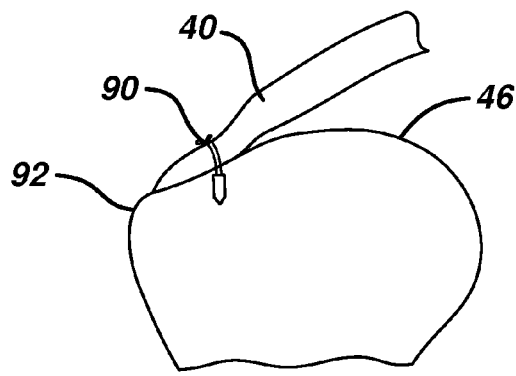
FIG. 11 is a side elevation of the tendon of FIG. 4 showing the suture limbs knotted together to compress the tendon to the humerus thus effecting repair of the PASTA lesion.

As seen in FIG. 9 a spinal needle 80 is passed through the tendon 40 at a second location 82 spaced apart from the first location 39. A flexible wire suture capture device 84 having a suture capture loop 86 (such as a Chia Percpasser available from DePuy Mitek, Inc. of Raynham, Mass.) is passed through the spinal needle 80 and retrieved out through the auxiliary cannula 78 so that the first suture limb 74 can be threaded through the suture capture loop 86. When the spinal needle 80 and suture capture device 84 are pulled back through the skin this pulls the first suture limb 74 through the tendon 40 at the second location 82. For a quick procedure, the first and second suture limbs 74 and 76 could now be knotted together tying down the tendon 40. However, it is preferable to repeat the procedure of FIGS. 8 and 9 with the second suture limb 76 to pass it through the tendon 40 at a third location 88 on an opposite side of the first location 39 as shown in FIG. 10. To ease in knot tying both suture limbs 74 and 76 are preferably pulled out through a single portal such as the auxiliary cannula 78 or other portal through the skin. A knot 90 can then be tied and pushed down to tightly secure the tendon 40 to the humeral head 46 as shown in FIG. 11. By passing the suture limbs 74 and 76 through the tendon 40 at locations 82 and 88 on opposite sides of the first location 39 and defect caused at that location via the passing of the cannula system 48 will be naturally pulled together when the knot 90 is tightened.

Depending upon the extent of the PASTA lesion it may be desirable to place more than one suture anchor 10 beneath the tendon 40. In such case the suture limbs therefrom can be tied together. It would still be preferable to pass the suture limbs through the tendon at separate locations as illustrated in FIGS. 9 and 10 prior to tying them together, preferably in a mattress pattern. One procedure utilizing two suture anchors is illustrated in FIGS. 16-20 below. Also, a repair could be fashioned employing one or more knotless suture anchors (not shown) such as disclosed in U.S. Published Application No. 2008/0033486 by Whittaker et al., incorporated herein by reference in its entirety, placed at a location 92 laterally of the tendon 40 and wherein the suture limbs 74 and 76 from the one or more anchors 10 can be passed in a dual row procedure, preferably also employing a mattress pattern. If a lateral anchor is employed, one such method is to put the a pair of present suture anchors 10 anterior and posterior and have one limb 74 from each tied to each other and the other limbs 76 spanned to the lateral anchor, preferably knotless, such that it forms a triangle.

The suture anchor 10 and cannula system 48 may also be used to effect repair of a SLAP (Superior labral tear from Anterior to Posterior) lesion. Typically a much larger traditional cannula (7-8 mm) is placed thru the rotator cuff to access the superior labrum for a SLAP repair. The present cannula system is much smaller and also due to its tendency to dilate the tissue rather than be inserted through a large slit would inflict less trauma to the rotator cuff. Such a procedure may be as follows: insert the K wire 38, and then the cannula system 48 in the fashion heretofore described through the rotator interval; drill a hole in the glenoid rim; insert the anchor 10; remove the cannula system 48; pass suture through the labrum using a suture shuttle; and tie knots.

The procedure is conveniently performed through a cannula system 48 which provides both access through the skin and through the tendon 40. The cannula system 48 is sized to just pass the anchor 10, not leaving much room for passing instruments to manipulate the tissue, especially the tendon 40. Although described in reference to the optimally narrow suture anchor 10, the cannula system 48 and method of penetrating soft tissue for anchor placement therewith are suitable for other anchors of larger size, as are other constructions of cannulas according to the present invention. For instance they could be employed with the HEALIX or GRYPHON anchors in sizes 4 mm and above available from DePuy Mitek, Inc. of Raynham, Mass.

Figure 12:
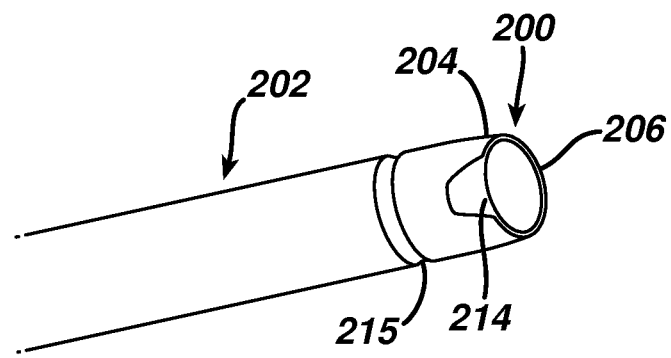
FIG. 12 is a perspective view of a distal portion of an alternative embodiment of a cannula according to the present invention.
Figure 13:
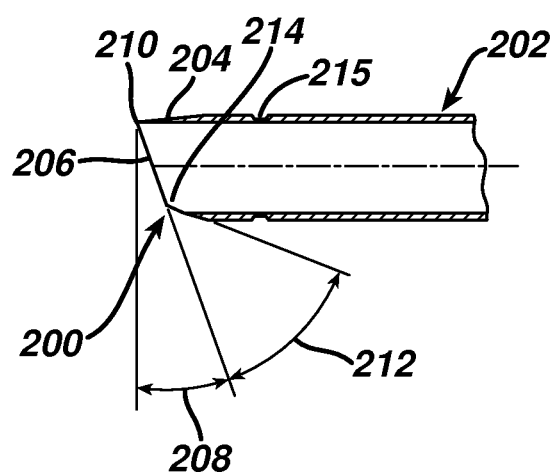
FIG. 13 is a side elevation view in cross-section of the distal portion of the cannula of FIG. 12.

FIGS. 12 and 13 show a distal portion 200 of an alternative embodiment of a cannula 202 according to the present invention which incorporates an ability to manipulate the tendon (not shown in FIGS. 12 and 13). At least the distal portion and shaft of cannula 202 are formed of a medical-grade, sterilizable metal such as a stainless steel material. The leading edge of distal portion 200 is ground on the outside to provide a slight annular chamfer 204 and create a sharp distal edge 206, preferably sufficiently sharp to be capable of cutting through a tendon. It is also asymmetric to assist in penetrating tissue. A first angle 208, preferably about 20 degrees, is ground across the portion 200 to create a sharper tip 210. A second angle 212, preferably about 45 degrees, is ground across a proximal portion of angle 208 to create a pair of points 214 which can engage the bone and help hold the distal portion 200 in position thereagainst. It can also assist in providing some cutting action if needed, especially if the cannula 202 is rotated as it is passed through tissue. An annular groove 215 about the outer surface of the cannula 202 sits proximal of the distal portion 200 and provides for tissue engagement which will be shortly explained. The term "groove" is intended to include elongated depressions, channels and other recesses.

Figure 14:
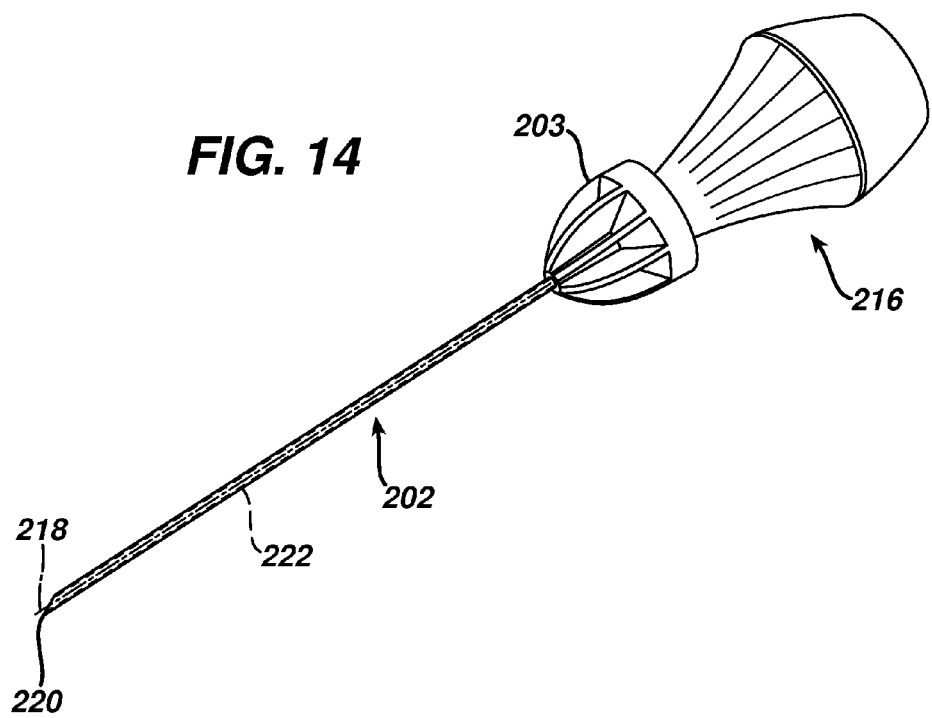
FIG. 14 is a perspective view of an obturator with the cannula of FIG. 12.

Turning also now to FIG. 14, an obturator 216 is sized to fit closely within the cannula 202 and mates with enlarged proximal collar or handle 203 of cannula 202 in this construction. Obturator 216 has a central axis 218 and terminates in a distal tip 220 which is laterally offset from the central axis 218 and is sharp in some constructions and blunt in other constructions. A central lumen 222 passes down the obturator 216 for receiving the K-wire (not shown in FIGS. 12-14). By making the tip 220 off-axis it is not interrupted by the lumen 222.

In practice, the cannula 202 and obturator 216 work similarly to the procedure described above. A K-wire, preferably with a trocar-type tip, is placed through the skin and tendon to engage the underlying bone at the position for placing the anchor (not shown in FIGS. 12-14). The cannula 202 with the obturator 216 therein and its distal tip 220 extending distally thereof is passed over the K-wire. The obturator distal tip 220 mostly dilates tissue as in passes along the K-wire, especially when distal tip 220 is blunt, and the chamfer 204 of cannula 202 likewise further dilates the tissue. Accordingly, the cannula 202 and obturator 216, rather than cut a cannula-sized hole out of the tissue, expand an opening through it while removing little tissue to create less damage to the tissue and ease healing of the tissue after the procedure.

Figure 15:
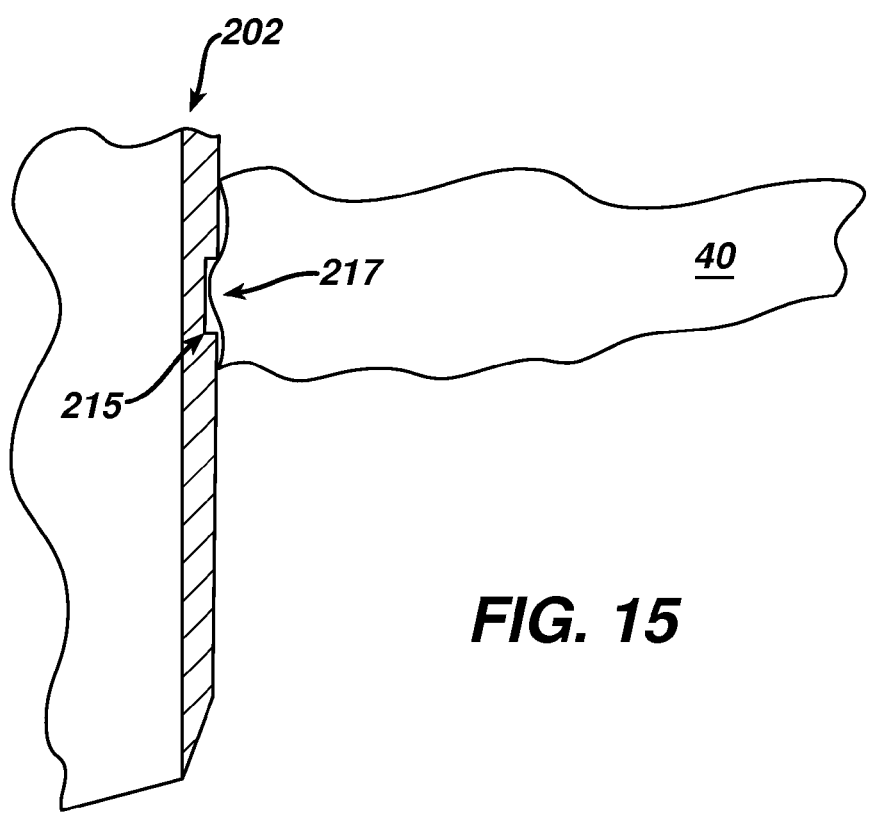
FIG. 15 is a partial side cross-sectional view of the distal portion of the cannula of FIG. 12 passing through and engaging a tendon for manipulation thereof.

Turning also now to FIG. 15, once the cannula 202 has penetrated the tendon 40 the groove 215 provides an engagement with the tendon 40 which tends to expand slightly into the groove 215, such as illustrated by tissue bulge 217, and catch sufficiently, yet gently, on the cannula 202 such that a surgeon can lift the tendon to enhance visualization of the bone underneath without damaging the tendon. The tendon 40 can be moved across the bone to a desired position if the surgeon wishes. The procedure is then completed as described above with an anchor being placed through the cannula 202. In other constructions, the tissue engaging feature is a raised rib or other projection. However, a type of groove is preferred instead of a projection to minimize trauma to the soft tissue. A projection may further dilate the tissue, and less tissue dilation is generally preferred.

Figure 16:
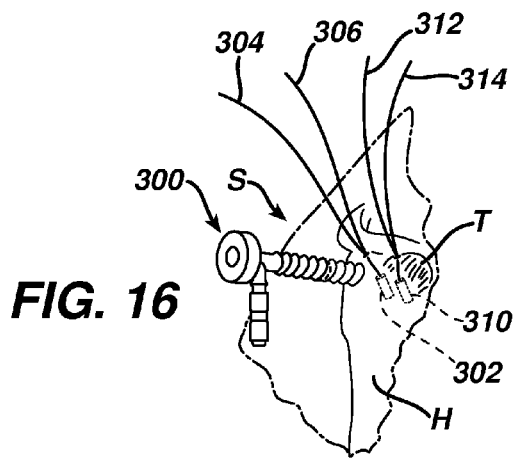
FIGS. 16-20 are schematic perspective views of two suture anchors, after being inserted into bone according to the present invention, with suture limbs being tied through a cannula to fixate a tendon in the shoulder of a patient.
Figure 17:
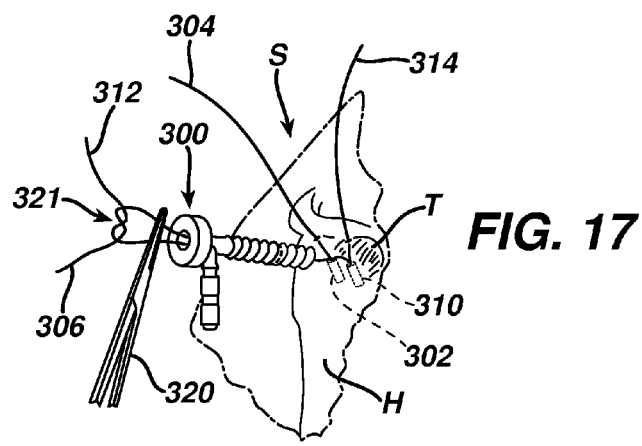
Figure 18:
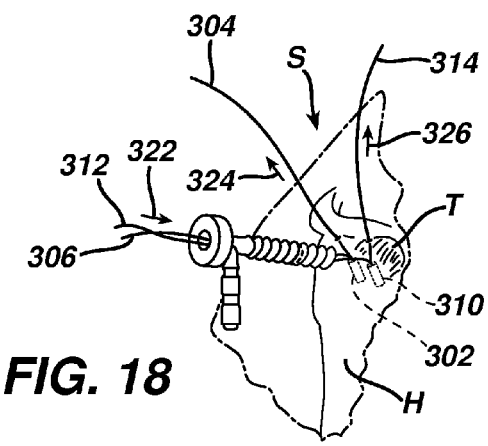
Figure 19:
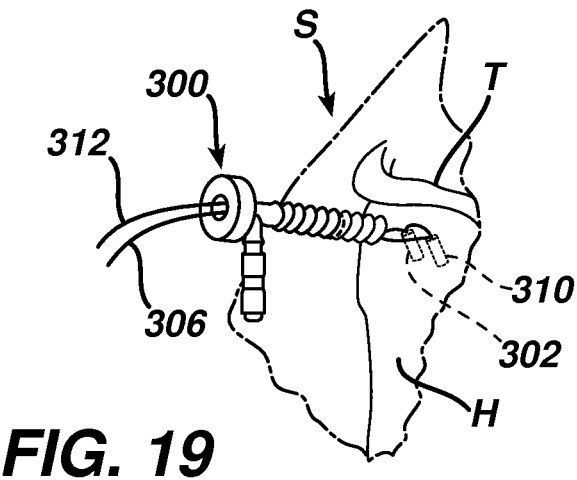
Figure 20:
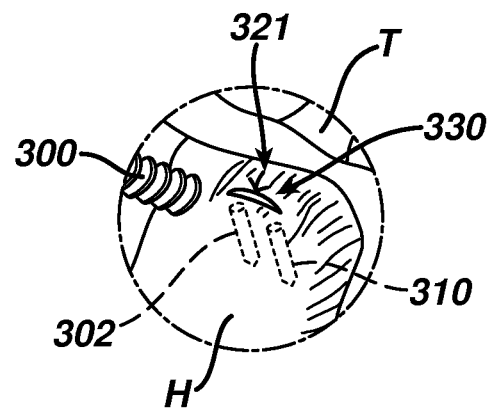

FIGS. 16-20 illustrate an alternative technique for repair of shoulder S utilizing at least two suture anchors 302 and 310, each of which preferably has been inserted through tendon T and into humerus bone H at two desired locations utilizing procedures described above. Anchor 302 slidably carries suture limbs 304 and 306 while anchor 310 carries suture limbs 312 and 314. An arthroscope (not shown) is placed in the subacromial space above the head of humerus H. Cannula 300, FIG. 16, is inserted laterally in the same portal used for subacromial decompression. One suture limb is retrieved through cannula 300 from each anchor, such as limbs 306 and 312, FIG. 17. A clamp 320 is placed on suture limbs and a knot 321 is tied against clamp 320. The knot 321 is then shuttled through cannula 300, as indicated by arrow 322, FIG. 18, by pulling on the other suture limbs 304 and 314 as indicated by arrows 324 and 326, respectively, until a desired tension on tendon T is achieved. Suture limbs 304 and 314 are then tied arthroscopically using a non-sliding knot to complete the repair with a suture bridge 330, FIG. 20, to fixate tendon T to humerus H. Excess suture may be removed with a cord cutter as desired.

Other systems according to the present invention ease insertion of a cannula through soft tissue by creating a small initial incision which is then expanded to create a portal, preferably trans-tendonous, to the desired repair location. Preferably, the cannula has multiple curved portions or sections which interact with one another to insert through tissue in a minimally invasive fashion and then are rotated or otherwise manipulated to create a full portal through soft tissue as desired.

In some constructions, a cannula system according to the present invention has multiple interacting thin-walled, preferably sharp-tipped sleeves, cylinders or tubes, also referred to as curved sections, which are partial-arcs in some constructions and substantially full-arc, full-circumference cylinders in cross-section spaced from their distal portions in other constructions. In an initial configuration, the distal portions of the tubes are aligned to present less than a full circumference of cannula to the soft tissue, such as to form a semi-circle, preferably substantially a half-circle or less, and inserted through soft tissue to form a "half-moon"-like, crescent-shaped incision or opening through the soft tissue. The cannula tubes are then manipulated to form a substantially circular portal through the soft tissue. Suture anchors or other devices or instruments can then be passed through the cannula system. After use is completed, the system preferably is collapsed or otherwise returned to its initial configuration and removed from the patient while minimizing trauma to the soft tissue. An initial low-profile, relatively small incision is thereby dilated by manipulating the cannula to form an arthroscopic portal.

Figure 21:
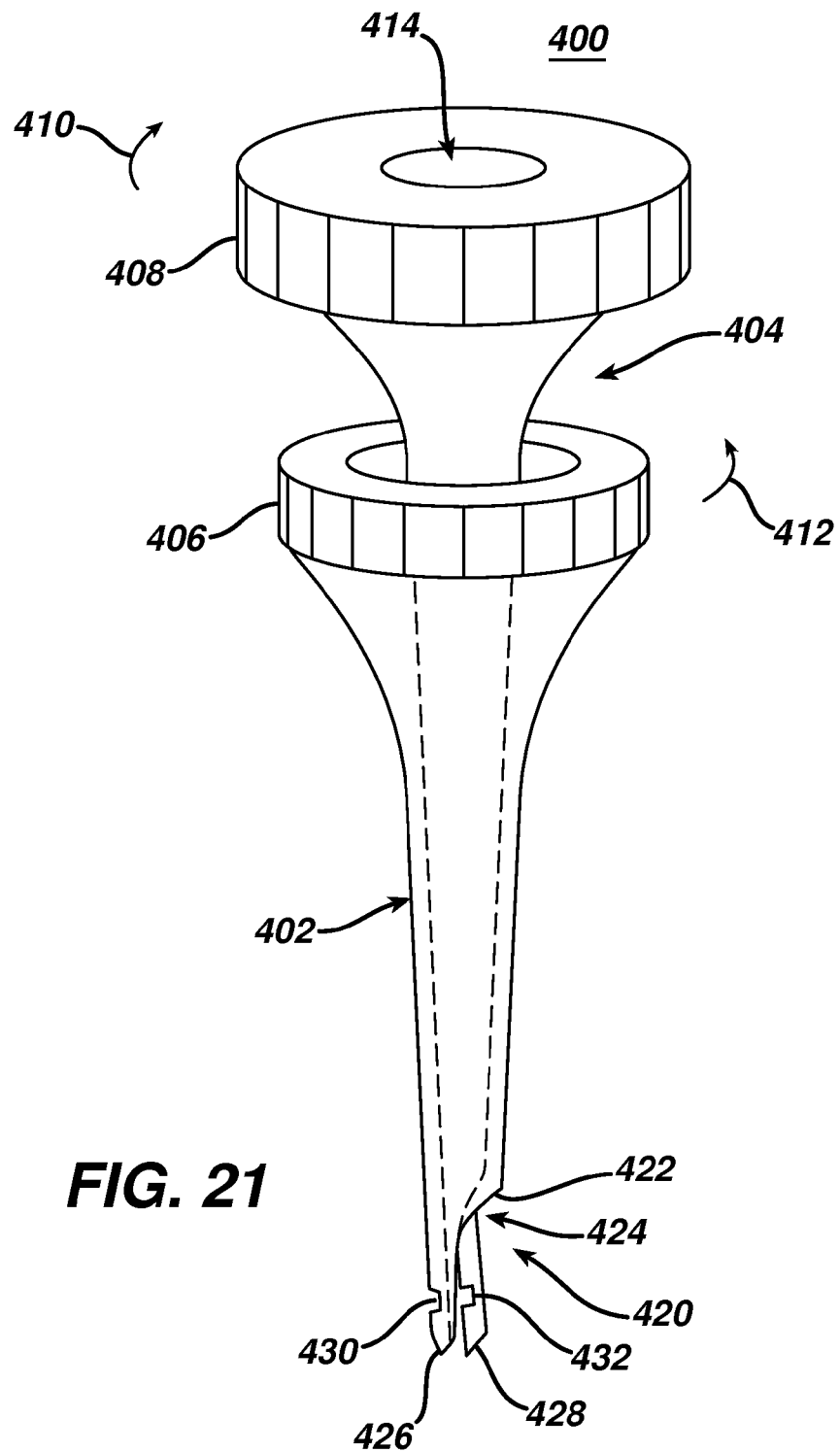
FIG. 21 is a schematic perspective view of a cannula according to the present invention having first and second curved sections which are rotatable relative to each other.
Figure 22:
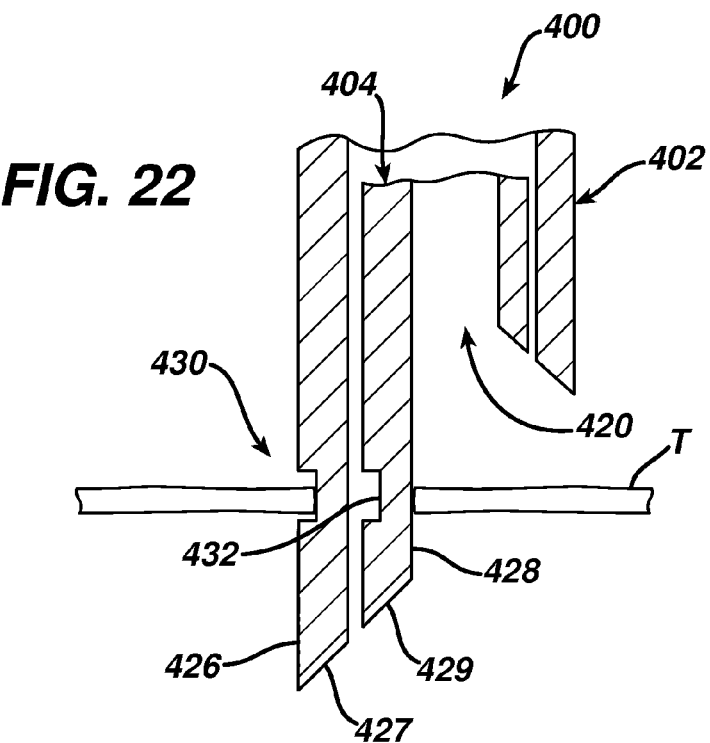
FIGS. 22 and 23 are schematic cross-sectional views of the distal portion of the cannula of FIG. 21 in first and second configurations relative to a tendon.

Cannula 400 according to the present invention, shown in an initial, low-profile configuration in FIGS. 21 and 22, has a first curved outer section 402 and a second curved inner section 404 which is generally coaxial with first section 402. Preferably, at least the shafts and distal portions of sections 402 and 404 are formed of a medical-grade, sterilizable metal such as a stainless steel material. A grip 406 of biocompatible material is positioned near the proximal end of first section 402 and a grip 408 is positioned near the proximal end of second section 404 to assist rotation, either manual or robotic, of the sections 402, 404 relative to each other as indicated by arrows 410 and 412. A proximal opening 414 is defined in second section 404 to communicate with an axially-extending cannula lumen 420. First section 402 has an angled or tapered distal portion 422 terminating in a distal end 426 with a beveled edge 427, shown in enlarged cross-section in FIGS. 22 and 23, and second section 404 has an angled or tapered distal portion 424 terminating in a distal end 428 with a beveled edge 429. In this construction, edges 427 and 429 are sufficiently sharp to be capable of cutting through a tendon. Also in this construction, both distal portions 422 and 424 define arcuate grooves 430 and 432, respectively.

Figure 23:
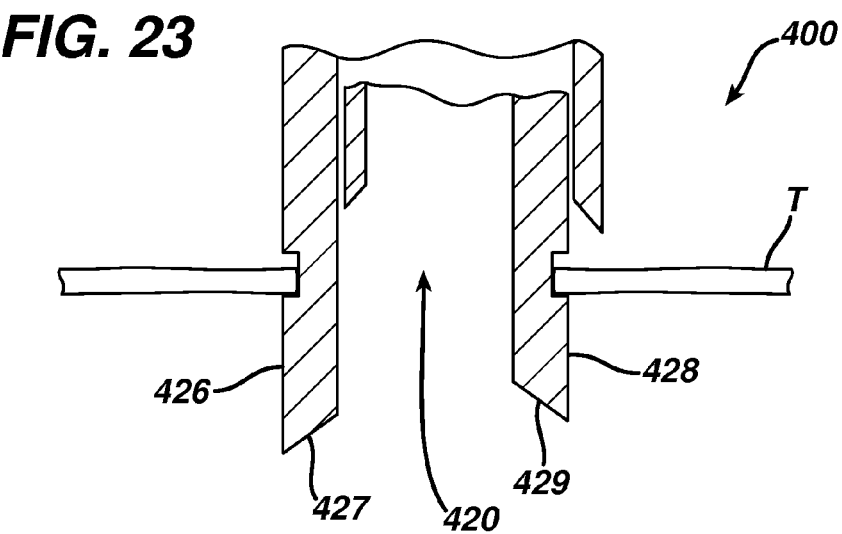
Figure 24A:
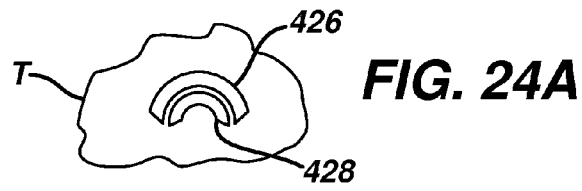
FIGS. 24A-C are schematic underside views of FIGS. 22 and 23.
Figure 24B:
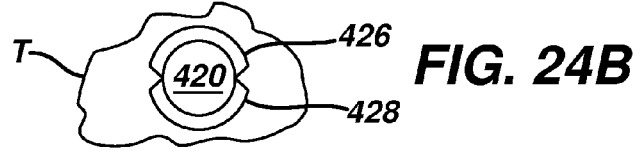

First and second sections of cannula 400 are shown in the initial configuration in FIGS. 22 and 24A relative to tendon T and in a second, expanded configuration in FIGS. 23 and 24B. Both the first and second distal portions progressively increase arcuately as measurable progressing away from distal ends 426 and 428, that is, both distal portions 422 and 424 have an angled distal surface to progressively increase the surface area of initial contact with the soft tissue. Tissue engagement feature 432 is covered in the initial configuration and is exposed in the expanded configuration to enhance contact with tendon T to facilitate manipulation of that tissue by a surgeon.

Figure 24C:
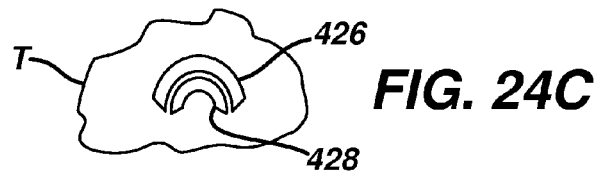

Preferably, sections 402 and 404 are returned to the initial configuration after access through and manipulation with cannula 400 has been completed, as illustrated in FIG. 24C. Further trauma to the soft tissue is thereby minimized as the cannula 400 is withdrawn from a patient.

Figure 25:
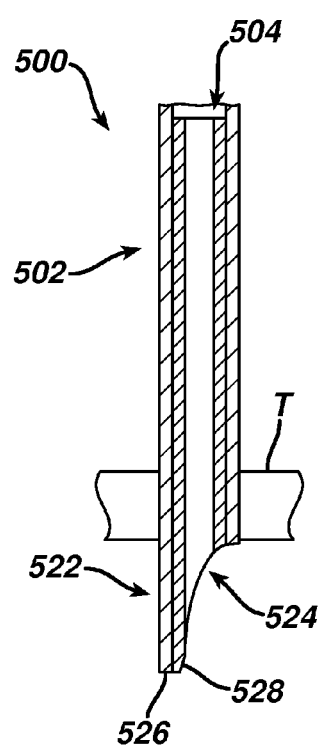
FIGS. 25 and 26 are schematic cross-sectional views of the distal portion of an alternative multi-section cannula according to the present invention.
Figure 26:
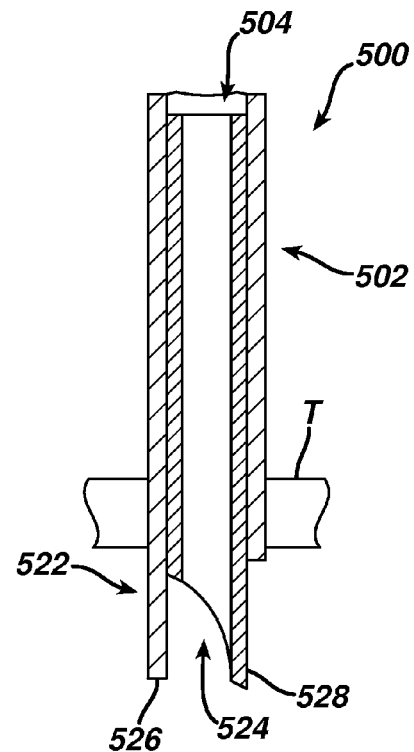

Alternative cannula 500 is shown in an initial configuration in FIG. 25 and in an expanded configuration in FIG. 26 having first curved section 502 and second curved section 504. In this construction, soft tissue T is fully dilated by the initial configuration as cannula 500 is passed through tissue T. While both the first and second distal portions 522 and 524 have an angled distal surface to progressively increase the surface area of initial contact with the soft tissue, only the second distal end 528 has a beveled edge in this construction. First distal end 526 is simply thin-walled.

Cannula systems according to the present invention have been described herein for use with rotator cuff repair including PASTA repairs and lesion repairs including SLAP repairs, but those are not limitations of the invention. Other suitable procedures for shoulder repair include biceps tenodesis, Bankart repair, acromio-clavicular separation repair, deltoid repair, capsular shift and capsulo-labral reconstruction. Suitable foot and ankle procedures include lateral stabilization, medial stabilization, Achilles tendon repair, mid-foot reconstruction, hallux valgus repair, metatarsal ligament and tendon repairs. Suitable knee procedures include medial collateral ligament repair, lateral collateral ligament repair, posterior oblique ligament repair, and ilio-tibial band tenodesis. Suitable elbow repairs include biceps tendon reattachment, ulnar and radial collateral ligament reconstruction, and lateral epicondylitis repair. Suitable wrist procedures include scapholunate ligament reconstruction, and suitable hip procedures include capsular repair and acetabular labral repair.

While the invention has been particularly described in connection with specific embodiments thereof, it is to be understood that this is by way of illustration and not of limitation, and that the scope of the appended claims should be construed as broadly as the prior art will permit. Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method for passing a suture anchor through a tendon and into a bone, the method comprising the steps of:
    locating a desired anchor receiving site on the bone;
    passing a locating wire through the tendon and at least onto the bone at the anchor receiving site;
    passing over the locating wire and through the tendon a cannula which comprises a thin-walled distal portion, and an axial lumen therethrough sized to accommodate at least the positioning wire;
    engaging a portion of the tendon with a tissue engaging feature on at least a portion of an outer surface of the cannula proximal of and adjacent to the distal portion and then manipulating the tendon with the cannula;
    passing the suture anchor through the cannula and placing the suture anchor into the bone at the anchor site; and
    wherein the step of manipulating the tendon comprises lifting the tendon away from the bone.

2. The method according to claim 1 wherein the step of manipulating comprises moving the tendon to enhance visualization underneath the tendon.

3. The method according to claim 1 and further comprising the step of attaching the tendon to the bone via a suture attached to the suture anchor.

4. The method according to claim 1 wherein the tendon is a rotator cuff tendon.

5. A method for passing a suture anchor through a tendon and into a bone, the method comprising the steps of:
    locating a desired anchor receiving site on the bone;
    passing a locating wire through the tendon and at least onto the bone at the anchor receiving site;
    passing over the locating wire and through the tendon a cannula including a first curved section having a first thin-walled distal portion and a second curved section having a second thin-walled distal portion, the first and second curved sections being positioned relative to each other in an initial, low-profile configuration with the second section nesting at least partially within the first section to present less than a full circumference of cannula to the tendon;
    moving the first and second curved sections relative to each other from the initial, low-profile configuration to a second, larger configuration defining an axial cannula lumen therethrough; and
    passing the suture anchor through the cannula and placing the suture anchor into the bone at the anchor site.

6. The method according to claim 5 wherein the cannula further includes a tissue engaging feature on an outer surface of at least one of the first and second curved sections of the cannula proximal of and adjacent to the distal portion, and the method further includes engaging a portion of the tendon with a tissue engaging feature on an outer surface of the cannula proximal of and adjacent to the distal portion and then manipulating the tissue with the cannula.

7. The method according to claim 6 wherein at least a portion of the tissue engaging feature is protected relative to the tissue in the initial configuration and is exposed to the tissue in the second configuration.

8. The method according to claim 6 wherein the tissue engaging feature is an arcuate groove on each of the first and second curved sections.

9. The method according to claim 6 wherein the tissue engaging feature comprises a groove.

10. The method according to claim 6 wherein the step of manipulating the tendon comprises lifting the tendon away from the bone.

11. The method according to claim 5 wherein at least one of the first and second distal portions has an angled distal surface to progressively increase the surface area of initial contact with the tendon.

12. The method according to claim 5 wherein at least one of the first and second distal portions has a distal edge which is sufficiently sharp to be capable of cutting through the tendon.

13. The method according to claim 5 and further comprising the step of attaching the tendon to the bone via a suture attached to the suture anchor.

14. The method according to claim 5 wherein the tendon is a rotator cuff tendon.

15. The method according to claim 5 wherein the step of moving the first and second curved sections relative to each other comprises rotating at least one of the first and second curved sections about a longitudinal axis through the cannula.

16. A method for passing a suture anchor through a tendon and into a bone, the method comprising the steps of:
    locating a desired anchor receiving site on the bone;
    passing a locating wire through the tendon and at least onto the bone at the anchor receiving site;
    passing over the locating wire and through the tendon a cannula which comprises a thin-walled distal portion, and an axial lumen therethrough sized to accommodate at least the positioning wire;
    engaging a portion of the tendon with a tissue engaging feature on at least a portion of an outer surface of the cannula proximal of and adjacent to the distal portion and then manipulating the tendon with the cannula;
    passing the suture anchor through the cannula and placing the suture anchor into the bone at the anchor site; and
    wherein the tissue engaging feature comprises a groove.

* * * * *